United States Patent [19]

Chrambach et al.

[11] 4,139,440

[45] Feb. 13, 1979

[54] ELECTROFOCUSING IN BUFFERS

[75] Inventors: Andreas Chrambach, Bethesda; Nga Y. Nguyen, Kensington, both of Md.

[73] Assignee: Government of the United States, Washington, D.C.

[21] Appl. No.: 808,378

[22] Filed: Jun. 20, 1977

[51] Int. Cl.² ............................................. G01N 27/26
[52] U.S. Cl. .......................... 204/180 G; 204/180 R; 204/299 R; 23/230 B; 424/12
[58] Field of Search ........... 204/180 G, 180 R, 180 S, 204/299; 23/230 B; 424/12

[56] References Cited

U.S. PATENT DOCUMENTS

| | | | |
|---|---|---|---|
| 3,607,695 | 9/1971 | Schneider | 204/180 S |
| 3,664,939 | 5/1972 | Luner et al. | 204/180 R |
| 3,687,833 | 8/1972 | Parcells et al. | 204/180 G |
| 3,770,603 | 11/1973 | Grubhofer et al. | 204/180 G X |
| 3,901,780 | 8/1975 | Denckla | 204/299 X |
| 3,912,609 | 10/1975 | Arlinger | 204/180 R |
| 3,960,499 | 6/1976 | White | 204/180 G X |

*Primary Examiner*—Arthur C. Prescott
*Attorney, Agent, or Firm*—Holman & Stern

[57] ABSTRACT

Methods of electrofocusing in amphoteric or non-amphoteric buffers is disclosed. In such methods, buffers are employed as carrier constituents, and optionally as anolyte and catholyte. Using a buffer electrofocusing system, stability with time has been achieved for a natural pH gradient.

5 Claims, No Drawings

ELECTROFOCUSING IN BUFFERS

BACKGROUND AND SUMMARY OF THE INVENTION

The present invention relates to electrofocusing the buffers. More particularly, the present invention is concerned with electrofocusing in amphoteric or nonamphoteric buffers, and with the achieving of stability with time for a natural pH gradient.

The concept of pH gradient electrophoresis has been previously considered to include the formation of a natural pH gradient due to the attainment of the isoelectric state by amphoteric compounds of a wide variety of isoelectric points. In this view of isoelectric focusing, subsequent to a relatively short transient state, in which the ampholytes approach their isoelectric positions within the pH gradient, an "equilibrium" state of long duration ensues. The stable pH gradient may then serve to focus proteins at their isoelectric positions.

The foregoing isoelectric theory has been unable to explain three facts: (1) The instability of pH gradients formed with Ampholine as a function of time, with simultaneous migration of first the basic, then the neutral, then the acid carrier ampholytes into the cathode chamber. Ampholine (or Servalyt under various trademarks) is the trade name for commercial amphoteric buffers comprised of synthetic mixtures of branched aliphatic polyamine carboxylates or sulfates.

This deterioration has been shown independently in polyacrylamide gels and in sucrose density gradients. It was not due to electroendosmosis; (2) The maintenance of a small, but finite current at the "steady-state"; and (3) The isoelectric focusing of nucleic acids.

These problems led to a consideration as to whether the pH gradient formed in focusing was not possibly identical to that formed within a stack. Therefore the buffers customarily used in polyacrylamidegel electrophoresis (PAGE) in multiphasic buffer systems (multiphasic zone electrophoresis, MZE) were tested for their ability, when mixed together at random, to yield stable pH gradients under the conditions of isoelectric focusing (IF) except for the absence of Ampholine. The success of this test led to testing of the suitability of nonamphoteric buffers as well. These experiments, indicative of the nonisoelectric nature of pH gradient formation in isoelectric focusing, are described in detail hereinafter.

DESCRIPTION OF THE PREFERRED EMBODIMENTS

EXAMPLE I (A). A mixture of 16 and 23 S ribosomal RNA. This mixture had been isolated by phenol extraction of ribosomes, precipitation of the RNA with 2 M LiCl, and final precipitation of redissolved RNA with alcohol. The mixture consists of about 70% 23 S and 30% 16 S RNA. Bovine serum albumin (BSA) was colored blue by addition of bromphenol blue. Hemoglobin (Hb) was obtained as fresh hemolysate at a concentration of approximately 50 mg/ml.

(B). Amphoteric buffer mixture. A 0.4 M solution of each of the following buffers was made: morpholinoethane sulfonic acid (MES: $pK_2=6.41$); morpholino-3-propanesulfonic acid (MOPS: $pK_2=7.2$); (N-2-acetamido-2-aminoethane) sulfonic acid (ACES: $pK_2=7.34$); N-tris (hydroxymethyl)-methyl-2-aminopropane-sulfonate (TES: $pK_2=7.96$); N-tris(hydroxymethyl)methyl-glycine (TRICINE: $pK_2=8.60$); N,N'-bis(2-hydroxyethyl)glycine (BICINE; $pK_2=8.74$); asparagine ($pK_2=9.00$); taurine ($pK_2=9.70$); glycine ($pK_2=10.46$); $\gamma$-aminobutyric acid (GABA: $pk_2=11.33$). All buffers were commercial grade.

(C). Nonamphoteric buffer mixture. A 0.4 M solution of each of the following was made: pyridine ($pK=5.5$); 4-picoline ($pK=6.2$); bis-(2-hydroxymethyl-imino-trishydroxymethyl)methane (BISTRIS; $pK=6.88$); 2,6-dimethylpyridine (lutidine; $pK=7.0$); imidazole ($pK=7.46$); hydroxyethylmorpholine (HEM; $pK=7.19$); N-ethylmorpholine (NEM; $pK=8.03$); triethanolamine (TEA; $pK=8.35$); tris (hydroxymethyl) aminomethane (TRIS; $pK=8.84$); monoethanolamine (MEA; $pK=10.35$). NEM, HEM, MEA, and TEA were redistilled in vacuo.

(D). Procedure of focusing. Focusing was carried out in an all-Pyrex PAGE apparatus using the insert for 6-mm i.d. tubes. The cathode chamber contained 0.2 M KOH, the anode chamber 0.2 N $H_2SO_4$. Gel concentration was 5%T, 15% $C_{DATD}$ for RNA and 10%T, 2%C Bis for BSA-Hb.

With regard to the abbreviations employed, %T = acrylamide (g) + cross-linking agent (g) /100 ml; %C = cross-linking agent (g) × 100/acrylamide (g) + cross-linking agent (g); DATD = N,N'-diallyltartardiamide, Bis = N,N'-methylene-bisacrylamide.

Polymerization and electrophoresis followed the procedures as described previously in Chrambach et al., *Methods of Protein Separation: A Modern Survey* (Catsimpoolas, N.ed.) Plenum, New York and in Rodbard et al., *Anal. Biochem.*, 40, 95 (1971). These procedures were carried out at 0°–5° C. A regulated current of 1mA/tube was maintained until the voltage reached 200V. Thereafter, a regulated potential was maintained at 200V. At the intervals specified below, tubes were withdrawn from the apparatus, and the gels were sliced into 1-mm sections. These were suspended in 0.5 ml of 0.02 M KCl, stored overnight in an evacuated desiccator over NaOH to remove $CO_2$, and analyzed for pH. Proteins or nucleic acid were loaded on top of the gel in the manner previously described for PAGE, and the gels were stained for protein by the procedure of Diezel et al., *Anal Biochem.*, 48, 617 (1972) or sliced and analyzed for RNA spectrophotometrically at 260nm.

(E). Procedure of isotachophoresis. Isotachophoresis was carried out in a lower buffer reservoir of 60-cm length as described, for example, in Baumann et al., *Proc. Nat. Acad. Sci. USA*, 73, 732 (1976), in gels of 10%T, 2%$C_{Bis}$ using MZW buffer system 2950 (phase BETA) at a final ionic strength of 0.01. The mixture of 0.04 M amphoteric buffers was loaded at 10.25, and 50 $\mu$l/6-mm-diameter gel and subjected to PAGE at 1-2 mA gel. After steady-state stacking was attained as judged by the formation of sharp leading and trailing edges and by the maintenance of constant stack width, the part of the gel containing the stack was subjected to IF for another 25 hrs. between acid anolyte and basic catholyte as described in Section (D). Analysis of pH within the stack was carried out after isotachophoresis on a duplicate gel, and after focusing of the isotachophoresis gel between $H_2SO_4$ and KOH.

Graphs were prepared showing the pH gradients formed in gels containing the amphoteric buffer mixture at concentrations of 0.001, 0.01 and 0.1M as a function of time of focusing. The most stable gradients were obtained at 0.1M of each of the constituent buffers.

Graphs were also prepared to show the rates of decrease of the current at constant voltage.

The focusing of bovine serum albumin (BSA) and hemoglobin (Hb) in the pH gradient formed by 0.1M amphoteric buffers was observed. The two proteins were found to achieve a steady-state position within 0.1 pH unit of their isoelectric points of 4.8 and 7.0, respectively. A second BSA band presumably appears since a 10% T, 2% C gel retards BSA oligomer sufficiently to prevent it from reaching the steady-state position of the monomer.

It was also observed that a 16 S ribosomal RNA, in a manner similar to non-amphoteric buffers, does not migrate off the gel. Although in the time investigated it does not reach a fixed steady-state position in the pH gradient, it does approximate such a position on the pH gradient between pH 4.67 (19hr) and 5.54 (68hr).

A graph was prepared showing the pH gradients formed with 0.1M nonamphoteric buffers. The rates of decrease of the current at constant voltage were also shown.

The amphoteric buffer mixture (0.4-2.0 $\mu$mol) was loaded onto a stacking gel (system 2950, I=0.01) together with 1mg of hemoglobin. After attainment of the steady-state by the criteria previously described, the stack was sliced and analyzed for pH. A graph was prepared showing the pH gradient within the stack. A duplicate stack was then placed between acid anolyte and basic catholyte (0.2 N $H_2SO_4$ and KOH) and focused for 25 hrs. The gel was then sliced and analyzed for pH. The resulting pH gradient was presented in graph form. It was found that the sigmoidal pH gradient across the stack in the particular buffer system used (pH of inflection =9.3) was maintained after the stack had been focused between acid anolyte and basic catholyte for a further 25 hrs. (final pH of inflection =9.0). Also, the position of the pH gradient on the gel was maintained. However, the buffer constituents in the mixture migrating at the leading edge of the stack, or ahead of the stack, formed the complete buffer pH gradient between pH 9 and 2 in the space left to them, between the leading edge of the stack and the acid anolyte. This pH gradient has the same extent as that formed by the same amphoteric buffer mixture throughout a control gel. It was concluded that the maintenance of a pH gradient within a stack, when this stack is being focused between acid and base, is compatible with the concept that during focusing the order of buffer constituents is maintained and that therefore focusing is basically steady-state stacking within a "pH-cage."

The foregoing Example has shown the following: (1) the possibility of forming stable pH gradients between acid and basic catholyte and anolyte, when the synthetic mixtures of amphoteric buffers known by their commercial name as Ampholine or Servalyt are replaced by simple buffers; (2) the possibility of forming stable pH gradients under the same conditions, except using non-amphoteric buffers; and (3) the possibility, based to date on indirect evidence, that a stack in MZE when placed between acid anolyte and basic catholyte in the field provides a stable pH gradient and a focusing system.

With regard to the first point, the demonstration that simple buffers can replace Ampholine in focusing is neither particularly surprising nor spectacularly original in view of the fact that amino acids and other simple buffers (Table 4 of Svensson, *Acta. Chem. Scand.,* 16, 456 (1966)) were used for focusing, e.g., Jonsson, M. and Pettersson, E. *Science Tools,* 15, 2 (1968) and Pettersson, E. *Acta. Chem. Scand.,* 23, 2631 (1969) prior to the synthesis of Ampholine described by Vesterberg, *Acta. Chem. Scand.,* 23, 2653 (1969). This finding may, however, become of practical value if it should be possible, by proper selection of pK and pI values and by due consideration of pI-pK, to assemble buffer mixtures yielding a linearity of pH gradient comparable to presently available Ampholine.

The finding of instability with time of amphoteric buffer pH gradients is also of interest since it rules out one of the hypotheses advanced to explain the instability of Ampholine pH gradients, viz., that it is due to chemical instability of Ampholine during focusing, or that it is related to a relative deficiency of Ampholine with neutral pI in the synthetic mixture. It should be noted in this context that the amphoteric buffer pH gradient, like the pH gradient produced by Ampholine, exhibits the progressive acidification of the gel with time, starting at the anodic end. It remains to be seen whether it also exhibits a migration of ampholytes into the catholyte reservoir, as observed with Ampholine.

As to the second point, the finding that non-amphoteric buffers, placed in the field between acid anolyte and basic catholyte, can produce stable pH gradients is novel and of profound importance for the theory of isoelectric focusing. In fact, it is this finding which suggests that pH gradient formation by focusing is nonisoelectric.

Concerning the third point, the hypothesis that some or all focusing may be nonisoelectric gives rise to a second hypothesis, viz., that focusing is steady-state stacking or isotachophoresis under conditions such that the buffers used as anolytes and catholytes in MZE are replaced by acid and base, thereby providing a "pH-cage" which by uncharging of the buffer through protonation or deprotonation and operation of the electroneutrality principle prevents the stack from migrating out of the gel. This hypothesis utilizes the fact that the theory of MZE predicts a pH gradient across a stack or, more precisely, a series of step-functions of pH, where each step corresponds to a single buffer (or protein or Ampholine component) aligned, at the steady state, within the stack in order of constituent mobility. Such orientation has recently been demonstrated for proteins. This hypothesis is at least indirectly supported by the fact that the pH gradient across a stack containing amphoteric buffers measured in this study, although very narrow, was maintained during focusing. A pH gradient across a stack containing Ampholine has been depicted previously, as shown in FIG. 2 of Chrambach et al., *Separat. Sci.,* 7, 785 (1972). Using a concentration gradient of stacking gel buffer, there has also been demonstrated such a pH gradient which, however, was not and would not be expected to be stable with time, as described by Chrambach et al., *Separat. Sci.,* 7, 725 (1972). To prove the hypothesis of orientation of constituents in order of mobility within a focusing system, it will be necessary to identify the relative positions of constituent buffers by use of direct chemical or isotope analysis for specific constituents: an order of mobility would indicate a stack; an order of pI, an isoelectric mechanism. Also, continuous scanning of the system during electrophoresis should enable one to distinguish between the characteristic shape of the distribution function of stacked in contrast to isoelectrically stabilized bands, if, as theory predicts, step-functions within a stack can be detected.

The concept that a stack may be immobilized by placement in the field between acid anolyte and basic catholyte corresponds to the mobilization of stationary isoelectric zones in IFPA by replacement of the anodic acid with buffers, which mobilization is being utilized at this time as a method of zone recovery in preparative IFPA.

As indicated above, buffer electrofocusing (BEF) is available as an alternative to isoelectric focusing in pH gradients formed by Ampholine. In both cases, the pH gradient is formed "naturally", i.e., by the electric field rather than use of a gradient maker. While, at this time, Ampholine pH gradients made of 50–500 amphoteric constituents excel in linearity of pH gradient over those made by as few as ten buffers, the buffer gradients appear to have advantages in temporal stability when made at high (0.1M) concentration, in two-dimensional electrofocusing-PAGE experiments and in the ease of staining, in addition to economic advantages. In principle, they also appear to have advantages in flexibility of gradient design, to suit the particular requirements of a fractionation.

As also discussed above, another theoretically important property of buffer pH gradients is that they can be made, although with imperfect linearity and with deviations from monotonic pH variation, by use of non-amphoteric buffers. An investigation was made, therefore, as to whether improved temporal stability or linearity could be obtained for pH gradients formed by a mixture of amphoteric and non-amphoteric buffers. While full elucidation of electrofocusing at the mechanistic level will necessarily be stepwise, and relatively slow, BEF in general, and the gradient made by non-amphoteric buffers in particular, provide a relatively simple tool for investigation of the mechanisms of electrofocusing, the types of bonds and the physical-chemical relations between carrier ampholytes or non-amphoteric buffers at the steady-state and in the two transient states of gradient formation and decay.

The foregoing has shown that the BEF gradients decay in a similar fashion to pH gradients established with Ampholine, thus ruling out Ampholine-specific reactions as the possible causes of gradient instability. The following discussion will show the additional similarity between Ampholine and buffer gradients in the progressive acidification of the gradient during gradient decay and in the cathodic drift of protein zones.

EXAMPLE II

The materials and methods employed were as follows:

(A). Proteins: A preparation of calf ovarian cAMP dependent protein kinase was obtained.

(B). Gel Buffer mixtures: (a) The amphoteric ("standard") buffer mixture was prepared as previously described. The standard gel buffer was modified by: (b) addition in equal proportions of the mixture of ten non-amphoteric ("basic") buffers prepared as described above; (c) addition to a final concentration of 0.1 M of pyridine ($pK_2=5.50$), picoline ($pK_2=6.21$), histidine ($pK_2=6.35$) and Bis- (2-hydroxy- ethyl)-imino-tris-(hydroxymethyl) methane (Bistris; $pK_2=6.88$); (d) addition of 0.1 M histidine, Bistris, lactic acid ($pK=3.84$) and propionic acid ($pK=4.86$).

(C). BEF in gel buffers a, b, c and d: BEF was carried out in gel buffers a, b, c and d in polyacrylamide gel of 10%T, 2%$C_{Bis}$. In BEF of the kinase preparation, a gel concentration of 5%T, 15% $C_{DATD}$ was used and preelectrofocusing (20 hrs. duration) preceded application of the proteins. Polymerization was carried out at 0°–4° C. in the Pyrex PAGE apparatus as previously described. Conditions of BEF were similar to those used previously in IFPA. Duration of BEF ranged from 16 to 186 hours. At various intervals, gel tubes were withdrawn from the apparatus, gels were sliced and allowed to diffuse into 0.5 ml of 0.02 M KCl overnight in vacuo over NaOH to adsorb $CO_2$ prior to pH analysis.

The results of these methods were as follows:

1. Modification of pH gradients in BEF by addition of 10 basic buffers to the standard amphoteric gel buffer mixture.

A pH gradient was formed in BEF, using as the Gel Buffer, a mixture between a standard assortment of amphoteric buffers and ten basic non-amphoteric buffers. Electrofocusing was carried out for 48 hours. The addition of the basic buffers: (a) extended the pH range covered by the "linear" pH gradient from (4.5–5.5) to (5.5–8.5);(b) caused the pH gradient to shift at the cathodic end from 6.5 to 9.5 while at the anodic end, the pH remained constant at 2.4–3.2; (c) shifted the linear segment of the pH gradient upward by 2–3 pH units; (d) did not improve the linearity of the pH gradient; and (e) caused the current to decrease, as a function of time, at a slower rate than observed with the standard buffers alone. The addition did not prevent, however, the attainment of a very low final current at the steady-state, suitable for BEF.

2. Modification of pH gradients in BEF by addition of two basic and two neutral buffers to the standard amphoteric gel mixture.

The addition of two basic and two neutral buffers to the standard amphoteric buffer mixture: (a) extended the pH gradient in the linear range from (4.5–5.5) to (5.8–7.5); (b) shifted the pH gradient at the basic end from 6.5 to 7.8 and maintained it at the acidic end at pH 2.4-2.2; (c) shifted the "linear" part of the pH gradient by 1.5 to 2 pH units upward; and (d) rendered the pH gradient more non-linear.

3. Modification of pH gradients in BEF by addition of two neutral and/or two acidic buffers to the standard amphoteric gel buffer mixture.

The addition of two neutral (histidine and Bistris) and two acidic (propionic and lactic acids) compounds to the standard gel buffer mixture: (a) extended the "linear" range of the pH gradient from (4.5–5.5) to (3.0–7.5); (b) reduced the linearity of pH gradient; and (c) shifted the pH gradient at the basic end from 6.4 to 7.8 and maintained it at the acidic end at pH 2.4-2.2. The addition of two acidic buffers (propionic and lactic acids) to the standard buffer mixture was without effect on the pH gradient.

4. pH gradient instability, progressive acidification and cathodic drift of protein in BEF.

BEF was conducted in gel buffer "d" for durations up to 112 hours and resulted in: (a) instability of pH gradient with time as previously observed; (b) progressive acidification with time, starting at the anodic end; and (c) progressive cathodic migration of proteins constituting the kinase preparation.

5. Reproducibility of pH gradients in BEF.

BEF was repetitively carried out, at different times, in the standard buffer mixture using a single duration of electrofocusing and also otherwise identical conditions. The pH gradients appeared reproducible within one pH unit, both with regard to the displacement along the pH axis and the slope of the pH gradient. The extent of the pH-range was constant.

As a result of such findings as shown in Example II, the pH gradients formed in BEF promised, in addition to economy, increased flexibility in the choice of both the pH-range and the slope of pH gradient. BEF also promised advantages of gradient stability, reproducibility and the applicability of fast "no background" protein staining procedures.

It appeared also of theoretical as well as of practical interest to investigate whether the properties of pH gradient decay observed in IFBA applied to BEF, particularly since deficiency of neutral Ampholine components or specific chemical instability of neutral Ampholine had been postulated by Baumann, G. and Chrambach, A. in "Progress in Isoelectric Focusing and Isotachophoresis", *Excerpta Medica,* (Amsterdam, 1975) pp. 13–23 as some of the possible causes of pH gradient instability.

With regard to the feasibility of improving the flexibility of electrofocusing by forming pH gradients in buffers, Ampholine preparations were found to provide a very limited number of pH ranges and relatively steep slopes of pH gradient. The possibility of producing stable pH gradients with buffers suggested the capability to generate a very wide variety of pH gradients of any desirable slope, tailored to the needs of any fractionation problem, by use of acidic, neutral and basic buffers as "pH gradient modifiers". The original pH gradients in BEF were very flat. They covered barely more than 1 pH unit in the linear range. Although such flat pH gradients may be desirable in some problems requiring maximal resolution, steeper gradients may be required in others. pH gradient "tailoring" may use: (a) for increasing the pH-range covered by the pH gradient — a basic or neutral buffer addition. In the representative cases observed, these shifts were of the order of 1–2 pH units per 15% to 50% increase in the number of buffer constituents; (b) for increasing the slope of the linear segment of the pH gradient — addition of neutral compounds, not that of basic and acidic compounds (at least in the cases tested). The magnitude of the effect is considerable. The slope increases by a factor of 5–6 upon a 15% addition of acidic buffer components; and (c) for vertically displacing a pH gradient along the pH scale, while maintaining a constant slope — the addition of basic buffer components, not that of acidic ones. In each case a 15 to 50% addition in the number of buffer components caused a pH shift covering 2–3 pH units.

As to a comparison of the characteristics of pH gradient instability relative to those observed in IFPA, the previous discussion showed that amphoteric buffer pH gradients, like the pH gradients produced by Ampholine, exhibited decay. This decay is now shown to also involve progressive acidification of the gel with time, starting at the anodic end, as well as a progressive cathodic drift of protein zones, again in complete analogy to Ampholine gradient. This excludes the hypothesis that Ampholine instability during electrofocusing, or deficiency of neutral Ampholine components, is a cause of pH gradient instability. Thus, the mechanism of electrofocusing conducted with buffers appears similar to that carried out with Ampholine.

With regard to the practical advantages of pH gradients formed in BEF, the finding that pH gradients formed in BEF exhibit most of the qualities of Ampholine pH gradients, with some advantages of Ampholine with regard to gradient linearity remaining, promises to be of practical value if they are reproducible and relatively stable with time. The previous study had already shown stability. These additional findings show that they are sufficiently reproducible, especially in the total range. This should allow one to carry out protein fractionation, in BEF, in the same fashion as in IFPA.

Staining of proteins in electrofocusing on polyacrylamide gels containing Ampholine has suffered from the fact that, to date, applicable "no background" protein procedures also stained the carrier ampholytes. It was therefore necessary in IFPA to diffuse the carrier ampholytes out of the gels, under conditions of protein fixation, before staining could be conducted. Alternatively, a stained Ampholine background had to be removed by a separate destaining procedure. Thus, in electrofocusing in Ampholine pH gradients (IFPA), one had the choice to either use a "no-background" stain with relatively poor sensitivity or a "background" procedure which was sensitive but required lengthy destaining. BEF is free of such dilemma. It is compatible with the sensitive "no-background" protein stains used in PAGE. However, a staining procedure for IFPA which recently appeared (Vesterberg et. al., *Biochim. Biophys. Acta,* 491, 160 (1977)) may annul this advantage of BEF.

Ampholine also interfered with protein staining and detection of reference boundary in two-dimensional IFPA-PAGE gels, as described by O'Farrell, P.H. in *J. Biol. Chem.,* 250, 4007 (1975). This difficulty is apt to disappear with the application of BEF to two-dimensional gel electrophoresis.

It is concluded that stable natural pH gradients formed with buffers provide advantages of flexibility in electrofocusing. They exhibit a sufficient degree of reproducibility to be useful for protein fractionation. They are compatible with fast, "no-background" staining procedures. Instability of pH gradients in BEF mimics that previously observed in IFPA with regard to rate, progressive acidification and cathodic drift of protein zones. The method promises advantages in two-dimensional electrophoresis.

EXAMPLE III

Isotachophoresis without spacers, designated as ITP-A, has been shown to have preparative importance, due to the high protein concentrations within the stack, brought about by operation of the "regulating functions".

ITP with Ampholine spacers, designated as ITP-C, in contrast has appeared to present difficulties of attaining the steady-state of ITP within the time and space limits allotted, at least when appreciable loads are applied. Also, Ampholine in the constituent mobility range suitable for spacing of protein zones is not available as yet.

Protein spacing by buffer zones, designated as ITP-B, and known colloquially as "cascade stacking" has been postulated. Using the Routs theory and program, as set forth in *Ann. N.Y. Acad. Sci.,* 209, 445 (1973), to compute the composition of ITP systems constituted by multiple zones of trailing buffer constituents (moving boundaries), ITP-B was set up and tested with regard to the maintenance of transient pH gradients, stacked zones and protein separation.

The possibility of obtaining pH gradients in electrofocusing with non-amphoteric buffers suggests a close relation, and possibly basic identity, between steady-state stacking and electrofocusing. Preliminary data has already shown that a narrow stack, formed by a single leading and trailing constituent, when transposed between acid and basic anolyte and catholyte, maintained pH gradient, sharp protein zone boundaries and relative protein band positions. Investigations were made of the stability of pH gradients and protein zone positions of a wide cascade stack subjected to electrofocusing. Similarly, to show full reversibility between stacking and electrofocusing, cascade electrofocusing was carried out to the steady-state, in the identical gel buffer mixture used to form the cascade stack, followed by ITP-B of the same gels, to demonstrate: (a) the degree of similarity between stable pH gradients in electrofocusing and the initial transient pH gradient in stacking: (b) relative absence of time dependent diffusion spreading of zones; and (c) maintenance of relative protein positions in the two separation procedures. The mobilization of focused bands as stacks by this procedure was also of practical interest as a preparative procedure.

The materials and methods employed were as follows:

(A). Hemoglobin was obtained as a hemolysate at a concentration of approximately 50 mg/ml. It was stored at 4° C. for not more than 2 weeks. Bovine serum albumin (Cat. No. A-4378; Sigma) was stained blue by addition of bromphenolblue. Ferretin (Cat. No. 900092; Schwarz/Mann) was obtained as a solution of 150 mg/ml. Phycoerythrin was an extract of *Ceramium rubrum*, obtained from Dr. H. W. Siegelman, Brookhaven National Laboratory, Long Island, N.Y. Stock solutions of Congo red (pI = 5.80) and methylblue (pI = 3.60) were prepared at a concentration of 0.1% in 5% aqueous ethanol.

(B). Buffer mixture used for ITP-B: a 0.05 M solution in 0.05 M Tris (Trizma Base, Sigma) of each of the following buffers was made: morpholinoethane sulfonic acid (MES; $pK_2$ = 6.41); (N-2 acetamido-2-aminoethane) sulfonic acid (ACES; $pK_2$ = 7.34); N-Tris-(hydroxymethyl) methyl-2-aminopropane-sulfonate (TES; $pK_2$ = 7.96); N-Tris-(hydroxymethyl) methyl glycine (tricine; $pK_2$ = 8.60); N,N'-Bis (2-hydroxymethyl) glycine (bicine; $pK_2$ = 8.74); glycylglycine (glygly; $pK_2$ = 8.94); asparagine ($pK_2$ = 9.00); taurine ($pK_2$ = 9.70); glycine ($pK_2$ = 10.46); γ-aminobutyric acid (GABA; $pK_2$ = 11.33). All buffers were commercial grade.

(C). Buffer mixture used for cascade electrofocusing: a 0.1 M solution in 0.05 M Tris of the above listed buffers was made, except that ACES was replaced by N-(2-acetamido)-2-iminodiacetic acid (ADA; $pK_2$ = 6.60 at 25° C.).

(D). Procedure of cascade stacking: ITP-B was conducted at 1°–5° C. in gels of 5%T, 15%$C_{DATD}$ in the multiple buffer system computed for this purpose ($pH_{MES}$ = 5.00). The PAGE apparatus was used with tubes of 6 mm I.D. The Lower Buffer was a solution of 0.625 M Tris in 0.050 N HCl. The Upper Buffer contained 0.048 M GABA and 0.01 M Tris. The Gel Buffer was 0.050 M MES, 0.002 M Tris. The mixture (50 μl) of the other 0.05 M buffers was loaded as a sample together with hemoglobin (0.5 mg), ferretin (1.5 mg), "blue BSA" (0.25 mg) and phycoerythrin. These standard proteins, both separately and mixed, were subjected to electrophoresis at 1 ma per tube. The formation of sharp leading and trailing zone boundaries, and the maintenance of constant band width with time were the criteria used to indicate the attainment of the steady-state. When the standard proteins were subjected together to ITP-B, buffer zones provided effective spacing between the proteins.

(E). Measurement of the pH gradient formed across the cascade stack: After the attainment of the steady state, tubes were withdrawn from the apparatus at suitable intervals. Gels were sliced into 1 mm sections. There were allowed to diffuse in 1 ml 0.02 M KCl overnight in an evacuated desiccator over NaOH to remove $CO_2$ and analyzed for pH.

(F). Transposition of ITP-B gels into an electrofocusing system: After 20 hrs of ITP-B, when the attainment of the steady-state was indicated by the criteria described in section (D) above, the gel was subjected to electrofocusing for 21 hrs between acid anolyte and basic catholyte at 1°–5° C. The gel was sliced and analyzed for pH as described in section (E).

(G) Procedure of cascade electrofocusing: Electrofocusing was carried out as described, for example, in Chrambach, et al., *Anal. Biochem.*, 42, 96 (1971) in gels containing the buffer mixture listed in section (C). The proteins listed in section (A) were loaded as a sample. The Gel Buffer contained 0.05 M MES, 0.002 M Tris. Gel concentration was 5%T, 15%$C_{DATD}$. Electrophoresis and pH analysis were carried out as described in section (E).

(H). Transposition of cascade electrofocusing gels into an ITP-B system: As soon as the pH gradient of the cascade electrofocusing gels (see section (G)) approached stability with time, the gels were transposed between the ITP Upper and Lower Buffers described in section (D) and electrophoresis was conducted for several hours at 1 ma per tube until the last band had migrated out of the gels.

The results of the methods of Example III were as follows:

1. Protein separation by cascade stacking: A buffer mixture which was computed using a program developed by Routs with multiple trailing constituents, provides multiple successive moving boundaries in electrophoresis. The leading constituent with the highest constituent mobility, as its salt with the common constituent, was added to the polymerization mixture (Gel Buffer). A mixture of the remaining buffers, at a concentration of approximately 0.05 M, was applied to the gel in the same fashion as a protein sample, together with several colored proteins, including hemoglobin, bovine serum albumin stained with brophenolblue, ferretin and phycoerythrin, and tracking dyes as moving boundary indicators. Electrophoresis was conducted for various times. Steady-state stacking was evidenced by: (a) the typical sharp zone boundaries of a stack; (b) the absence of significant band diffusion spreading as a function of time, characteristic for a stack at the steady-state; (c) the possibility to load 1000 times more protein into a well-defined band than possible in PAGE; and (d) the formation of a pH gradient across the stack.

2. Spacing of protein zones in a cascade stack by buffer zones: Hemoglobin and ferretin were subjected to cascade stacking (ITP-B). The resulting gel pattern was compared with that obtained by isotachophoresis without spacers of any kind (ITP-A). The moving boundaries constituted of buffers with constituent mobilities intermediate between ferretin and hemoglobin provide effective "spacing" in ITP-B.

3. The pH gradient formed within the cascade stack: a pH gradient formed across the stack in ITP-B with multiple moving boundaries. After the attainment of the steady-state as indicated by the formation of sharp zone boundaries, the gel was sliced and analyzed for pH at various stages of displacement of the stack towards the anode with the following results: (a) A fairly homogeneous pH gradient formed which coincided at all displacement distances with the extent of the stack recognized by sharp zone boundaries; (b) No stepwise variation of pH was found as would theoretically be expected to form between zones within a stack; (c) The pH gradient formed did not agree with that computed; (d) A uniform pH was observed after passage of the constituent with lowest constituent mobility through the gel, as a result of its entrance into the operative ZETA phase; (e) As the stack traversed the gel, the pH gradient broadened from 7.52 to 8.40 at its basic end but remained constant at pH 6 at the acidic end.

4. Relations between protein pattern and pH gradient in ITP-B before and after transposition of the ITP-B gel at the steady-state between acid and basic electrolytes, i.e., into an electrofocusing system: After attainment of the steady-state, a duplicate ITP-B gel was placed between acid anolyte and basic catholyte and electrofocused for 21 hrs with the following results: (a) The characteristic sharp moving boundaries of a stack were maintained; the protein zones moved along the pH gradient into their isoelectric positions (4.5 for ferretin, 7.3 for hemoglobin) and remained in these positions with time. The slope of the pH gradient remained approximately the same after transposition of the ITP-B gel between acid and basic electrolytes except that it shifted along the pH axis by about one pH unit towards more acidic values and that it "connected" to anodic and cathodic extremes of pH as previously observed.

5. Relations between protein pattern and pH gradient in cascade electrofocusing and those obtained after transposition of the cascade electrofocusing gel at the steady-state between Upper and Lower Buffers of the ITP-B system made up of the identical constituents as used in cascade electrofocusing: Electrofocusing of a mixture of the four proteins listed in section (A) was carried out in polyacrylamide gels containing a mixture of 0.05 M buffers computed as constituents of a ITP-B buffer system, $pH_{MES} = 5.00$. The pH gradient was analyzed at different intervals during electrofocusing. As soon as the pH gradient appeared to approach stability with time (17 hours), indicating the attainment of the steady-state, the gel was placed between Upper and Lower Buffers of the ITP-B system made up of the identical constituents as the leading and trailing phases of the system. Electrophoresis was continued. At various times, pH gradients and protein positions on the gel were measured. The pH gradients formed in cascade stacking and the positions of the colored proteins were graphed as a function of time. The sharply defined zones of the colored proteins obtained in cascade electrofocusing gels, the initial pH gradient, the order of proteins and constant band width with time were maintained as in cascade stacking. The zones with these properties of stacks moved progressively through the gel.

The results of Example III have implications for analytical and preparative gel electrophoresis, as well as for a theoretical understanding of electrofocusing.

1. The analytical and preparative usefulness of ITP-B with buffer spacers: ITP-A, without spacers, is a high load preparative tool for the separation of proteins differing predominantly in net charge, but it cannot be considered as an analytical method of protein fractionation, since the proteins with mobilities intermediate between the stacking limits align contiguously within the stack.

ITP with Ampholine spacers, designated as ITP-C, also presents difficulties as a generally useful analytical method for fractionation of proteins for different reasons: As the number of amphoteric components in an Ampholine preparation is relatively high, it may be difficult to reach the steady-state of stacking at high load levels within the limitations of time and space of an ITP experiment. Also, the constituent free mobility of the presently available Ampholine components, even with such a narrow pI-range as 8.00–8.15, in gels were found to be larger than mobilities representative for most proteins.

ITP with buffer spacers, ITP-B, is a new procedure of analytical and preparative protein fractionation which, although proposed by Jovin, T. M., *Ann. N.Y. Acad. Sci.*, 209, 445, 1973, has not previously been applied. In contrast to ITP-A, the characteristic sharp zone boundaries of proteins within the stack appeared separated by buffer zones with intermediate mobilities. This "buffer spacing" should allow one: (a) to carry out gram-preparative separations of proteins as have been demonstrated without buffer spacers avoiding boundary overlap as observed in ITP-A with a single moving boundary while maintaining the high load capacity due to the high "regulated" concentrations of all proteins and buffers migrating between the leading and trailing boundaries. Thus, ITP-B promises to be a highly effective preparative technique of protein fractionation; and (b) to be able, for the first time, to apply ITP effectively to protein separation at the analytical scale.

In application of ordinary steady-state stacking (ITP-A) to proteins, using single leading and trailing constituents, it is useful to obtain the closest possible fit between the constituent mobilities of the proteins of interest and the stacking limits of the particular MZE system. The selectivity and effectiveness of separation here is improved by narrowing of the stacking limits. In contrast, no such detailed optimization of stacking limits may be required in ITP-B; wide stacking limits can probably be used since the proteins will find their own place within the stack independently, to some degree, of mobility compartments with inappropriate stacking limits within the total stack.

2. Properties of the pH gradient in ITP-B: The stack containing multiple buffers exhibit a moving pH gradient wider than the stack containing a single set of leading and trailing constituents. Although in the present study there was no determination of the exact positions of the leading and trailing constituent buffers, from available evidence it appeared that the stack in ITP-B coincided with the region of sharply defined protein zones. As the moving boundaries were progressively displaced into the anodic reservoir, the pH gradient across the stack traversing the GAMMA phase gradually disappeared, giving rise to the constant pH of the operative PI or ZETA phase of the MZE system, of which the most slowly migrating constituent is the terminator.

The pH gradient formed in ITP-B does not extend towards extremes of pH as far as the computed pH gradient. The slope appears to be fairly smooth, showing no stepwise gradation as would be theoretically predicted.

3. The pH gradient in cascade electrofocusing: The pH gradient formed in cascade electrofocusing on polyacrylamide gel is stable with time of focusing as previously observed with different concentrations of various buffers. It was used to study reversibility between stacking and electrofocusing.

4. Fractionation by ITP-B followed by cascade electrofocusing: The pH gradient formed in ITP-B stabilizes with time after transposition of the ITP-B gel between strong acid and base. The slope of the pH gradient remains relatively unchanged after transposition of the ITP-B gel between acid and basic electrolytes. However, a shift of the pH gradient along the pH axis towards more acidic pH occurs. The characteristic sharp zone boundaries of a stack are maintained during electrofocusing and the order of alignment of the protein zones remains the same as in ITP-B. However, after transposition into a focusing system, protein bands are displaced along the pH gradient into their isoelectric positions.

5. Fractionation by cascade electrofocusing followed by ITP-B: Cascade electrofocusing gels, at the steady-state, when transposed between Upper and Lower Buffers of the ITP-B system formed with the identical buffers, maintain the sharply defined zones of the colored proteins as well as a constant band width with time, indicative of ITP at the steady-state. The order of proteins and buffers in cascade electrofocusing is the same as in ITP-B, at least in the case of the four proteins studied.

The mobilization of cascade electrofocusing zones by transposition between ITP Upper and Lower Buffers resembles that exploited previously for the purposes of zone elution in preparative IFPA.

It is concluded that the ITP-B and cascade electrofocusing appear fundamentally the same since: (a) cascade electrofocusing exhibits several of the characteristic properties of the stack in ITP-B, including zone sharpness, absence of time dependent diffusion and pH gradient; (b) the zones formed can be mobilized by transposition of the cascade electrofocusing gel into an ITP buffer system, with maintenance of constant zone width as a function of time, and with maintenance of a pH gradient which is initially similar to that in cascade electrofocusing. It progressively changes towards a final uniform pH characteristic for the PI phase; and (c) the stack in ITP-B can be immobilized by transposition of the stacking gel into an electrofocusing system; the pH gradient within the stack stabilizes and the order of zones and zone sharpness are maintained.

EXAMPLE IV

As an additional aspect of the present invention, it has been found that natural pH gradients can be formed in buffer electrofocusing when the strongly acidic and basic anolyte and catholyte are replaced by the "leading" and "trailing" buffers, possessing the lowest and highest $pK_2$ values, of the buffer mixture. High concentrations of sucrose (50%) in the anolyte and catholyte steepen the pH gradient. Also, high concentrations of anolyte and catholyte buffer (0.75 M) stabilize the pH gradient in buffer electrofocusing as a function of time.

In regard to this aspect, it is useful to consider the fact that electrofocusing comprises two stages: the formation of a natural pH gradient, and the stabilization of protein zones within such a gradient. Both remain unelucidated in their mechanisms. Until recently, it was assumed that both stages followed an identical mechanism involving "isoelectric condensation" of either carrier ampholytes or protein, with the strong acid and base on either side of the pH gradient forming a "pH cage" from which amphoteric compounds could not escape. However, two findings have raised doubt concerning such a unitary mechanism of electrofocusing, these being: (1) the apparently electrophoretic cathodic "drift" of Ampholine during electrofocusing, as described in Baumann, G. and Chrambach, A., Progress in Isoelectric Focusing and Isotachophoresis, pp. 13–23, Elsevier, Excerpta Medica, N. Holland, Assoc. Sci. Publ., Amsterdam (1975); and (2) the fact that natural pH gradients could be generated with non-amphoteric buffer, as described in Nguyen, N.Y. and Chrambach, A., *Anal. Biochem.*, 74, 145–153 (1976). Both findings suggest that formation and decay of pH gradients may involve chemical mechanisms quite different from "isoelectric condensation".

One possible contributory mechanism of pH gradient formation is that of steady-state stacking. Once the leading constituent of the stack is stopped in its migration by encounter, at the anolyte or catholyte, of a pH conductive to either uncharging it, if non-amphoteric, or making it isoelectric, if amphoteric, a stationary pH gradient may ensue. Transformation of the "extended stack" to an electrofocusing system has been demonstrated in indirect support of this concept.

It is also possible that a similar constituent arrest of the most basic or acidic constituent would prevent the migration of the other constituents into the electrolytes by acting as a zone of uncharged insulator, thus providing a necessary condition for the establishment of a pH gradient.

The immobilization of the "leading" constituent should occur at its isoelectric pH or, in the case of non-amphoteric constituents, at a pH providing zero net charge through protonation or deprotonation. Thus, it should be possible to form pH gradients between buffers of suitable pH, used as anolyte and catholyte. This hypothesis was investigated, using a simple system of buffer electrofocusing to form the pH gradient. The use of buffer anolytes and/or catholytes is not entirely original. Swanson and Sanders used it in conjunction with electrofocusing in Ampholine, as described, for example, in *Anal. Biochem.*, 67, 520–524 (1975). In contrast to the present invention, their buffers were not isoelectric or fully deprotonated, or protonated respectively. Consequently, their systems drew substantial currents, and exhibited abnormal rates of decrease of current with electrofocusing time. McCormick et al. used a buffer anolyte of a pH purposely higher than the anodic gel end, by an amount necessary to mobilize protein zones electrofocused at a particular pH, as discussed in *Anal. Biochem.*, 75, 314–324 (1976).

The materials and methods employed were as follows:

Buffer electrofocusing (BEF): BEF was carried out in polyacrylamide gels (5%T, 15%$C_{DATD}$, 0° C.). In application to the experiment reported as follows in the results, item No. 1, the gels contained the "standard amphoteric buffer mixture" reported previously in Nguyen, N.Y. and Chrambach, A., *Anal. Biochem.*, 74, 145–153 (1976) at a final concentration of 0.1 M in the gel. In all other experiments, the standard amphoteric or the non-amphoteric buffer mixture was made 0.04 M in distilled water, to give a final concentration of 0.01 M in the gels. Conditions of polymerization and of electrofocusing were those described previously in the same reference, except that in experiments with buffer anolyte and catholyte, a voltage of 650V was maintained after the initial rise of the voltage to that value at a regulated current of 1 ma/tube. The pH gradients were measured and recorded automatically, as described by Chidakel et al., *Anal. Biochem.*, 77, 216–225 (1977). All pH values reported refer to measurement at 25° C., and were not corrected for viscosity or ionic strength.

The results of the methods of Example IV were as follows:

1. Maintenance of pH gradients is possible in the absence of strongly acidic and basic anolyte and catholyte: a pH gradient was formed in buffer electrofocusing (BEF) with the standard amphoteric buffer mixture. The anolyte was 0.2 N $H_2SO_4$, the catholyte 0.2 N KOH. After attainment of the steady-state, the gel was transposed between 0.1 M solutions of the leading and trailing constituents of the buffer mixture, 2-(N-morpholino)-ethanesulfonic acid (MES), brought to pH 2.0 by addition of $H_2SO_4$, and $\gamma$-aminobutyric acid (GABA), pH 6.65, in substitution of $H_2SO_4$ and KOH. Electrofocusing was continued. Graphs were prepared, showing pH gradients as a function of time of electrofocusing between the two buffers, and, as a control under otherwise identical conditions, after gradient formation between acid and base. It was found that the pH gradients and the gradient decay rates were not significantly different between the two cases.

2. Formation of pH gradients in BEF, using amphoteric buffers, in the absence of strongly acidic and basic anolyte and catholyte: graphs were prepared, showing pH gradients formed in BEF with the standard amphoteric buffer mixture at 0.01 M concentration in the absence of strongly acidic and basic anolyte and catholyte. The leading and trailing constituents of the pH gradient, MES and GABA, 0.01 M, were used as anolyte and catholyte. The slope and extent of the pH gradient did not appear to be significantly different from the central linear portion of the pH gradient formed between $H_2SO_4$ and KOH under comparable conditions. However, when strong acid and base electrolytes were used, both ends of the central, linear portion of the pH gradient connected, across gradient endings with a much steeper slope, to the pH in the reservoirs.

3. Stabilization of the pH gradient in BEF by an increase in anolyte and catholyte buffer concentration to 0.75 M: Increase in the concentration of MES and GABA in the anolyte and catholyte reservoirs to 0.75 M stabilized the pH gradient formed with 0.01 M buffers in BEF under the conditions described in item No. 2. The relative stabilization of pH gradient obtained through use of highly concentrated electrolytes was, however, not absolute, i.e., gradient decay was slowed down but not abolished.

4. Steeping of the pH gradient in BEF by making the anolyte and catholyte buffer solutions 50% in sucrose: When the buffer anolyte and catholyte were made 50% in sucrose, the pH gradient steepened. However, the addition of 50% sucrose to the electrolyte reservoirs did not appear to repress the pH gradient decay. The admixture of sucrose to the gels as well as to the electrolytes seemed to be without effect on the slope or decay rate of the gradient or the rate of the decrease of current. The addition of 50% sucrose to 0.2 N KOH and $H_2SO_4$ in BEF with a 0.01 M amphoteric buffer gel also appeared to extend the pH gradient along the pH axis, thereby steepening the gradient.

5. Formation of pH gradients in BEF, using non-amphoteric basic buffers, in the absence of strongly acidic and basic anolyte and catholyte: graphs which were prepared showed that gels containing the 0.01 M non-amphoteric, basic buffer mixture electrofocused between the 0.01 M leading buffer, pyridine, and the trailing buffer, monoethanolamine, gave rise to a pH gradient. The quality of the gradient appears improved compared to non-amphoteric buffer pH gradients previously shown. As a control, the gel containing non-amphoteric buffers was electrofocused between 0.2 N KOH and $H_2SO_4$. The gradient stability and mechanical stability of the gels electrofocused between pyridine and monoethanolamine was better than that observed in the control experiment between acid and base or that in previous reports.

The results of Example IV are considered to be indicative of the following:

1. Simplification and potential improvement of resolving capacity of electrofocusing: The replacement of strongly acidic and basic anolyte and catholyte by the leading and trailing buffers provides a simplified buffer electrofocusing system for the physical-chemical investigation of pH gradient formation. In the practice of electrofocusing, the system using buffer anolyte and catholyte provides a flat pH gradient across the entire gel, through elimination of the "connections" of the pH gradient to the extremes of pH in the reservoirs. Flattened pH gradients should provide better resolution.

2. Improved stability of pH gradients: The relative stabilization of pH gradients through an increase in the concentration of buffer anolyte and catholyte is an important practical result for fractionation by electrofocusing. It provides an additional tool for stabilization to that obtained through an increase in gel buffer concentration.

3. Gradient steepening: Gradient steepening has previously been demonstrated in BEF, utilizing the addition of acidic and neutral buffers to the standard gel buffer mixture. The possibility to achieve the same end by increasing the sucrose concentration in the anodic and cathodic reservoirs adds to the flexibility of pH gradient design in BEF. No significantly different result was obtained when 50% sucrose was admixed to the gel, in addition to its use in the electrolyte buffers.

4. Mechanistic consequences of the use of buffer anolyte and catholyte: Natural pH gradient formation can no longer be pictured in terms of the "migration reversal hypothesis" alone, according to which amphoteric compounds upon contact with strong acid and base change their net charge and reverse their direction of migration, presumably coming to an isoelectric restpoint through an oscillatory migration path. Rather, it appears that the zones of "leading" and "trailing" constituents, maintained at isoelectric pH's by the anolyte and catholyte of identical composition, form a barrier to the passage of the "internal" constituents, either by "regulation" to zero mobility, or by operation of the laws of electroneutrality and conservation of mass analogous to that giving rise to the "regulating functions" in steady-state stacking. Such a mechanism should equally apply with amphoteric or non-amphoteric buffers, and with buffer anolytes and catholytes of appropriate pH as well as with the strongly acidic and basic anolytes and catholytes heretofore employed.

5. Cathodic drift: The isoelectric or uncharged "leading" and "trailing" constituents at the termini are in equilibrium with charged species. Their migration into the adjacent electrolyte may be the cause of pH gradient instability. It was attempted to depress the dissociation reaction of the constituents at the pH gradient termini, to decrease the concentration of these charged species, by increasing buffer concentration and viscosity (sucrose concentration) in the anolyte and catholyte. Only the increase in buffer concentration had a stabilizing effect, while the increase in viscosity failed to exhibit it, suggesting that the cathodic drift is due, wholly or in part, to the postulated mechanism. However, the use of buffer electrolyes makes it unlikely that the cathodic drift is due to a chemical instability of carrier ampholytes reacting at the termini with strong acid and base, or that electrolysis products of carrier ampholytes produced at extremes of pH would be responsible as postulated previously.

EXAMPLE V

As a further aspect of the present invention, pH gradients in buffer electrofocusing on polyacrylamide gel (BEF) have been stabilized for at least 100 hours, 25° C., by replacing the strongly acidic and basic anolyte and catholyte with isoelectric buffers identical to the terminal constituents of the pH gradient and gel. Such stabilization leads to a constand pI-position of an electrofocused protein. No stabilization of pH gradients is achieved under otherwise identical conditions when strongly acidic and basic anolyte and catholyte are used.

Isoelectric focusing was originally conceived as a steady-state method of protein separation, comprising a stable pH gradient and attainment of a steady-state position on such a pH gradient by the protein. However, pH gradients turned out to be labile in proportion to time and voltage, both in polyacrylamide gel and in sucrose density gradients, and whether the pH gradients were formed by Ampholine, amphoteric buffers, non-amphoteric buffers or aminoacids. In the practice of electrofocusing, this instability put a time limit on the attainment of a steady-state pH and of optimal resolution in electrofocusing, making it imperative to minimize molecular sieving effects which would unduly retard the protein migration rate. The mechanism of pH gradient instability remained unknown, although it could be shown that Ampholine migration, preponderantly into the cathode chamber, and a progressive acidification of the gel in the cathodic direction accompanied pH gradient decay, and that the Ampholine transport could not be accounted for by electroendosmosis or diffusion.

The possibility to generate natural pH gradients with non-amphoteric buffers and the "triplet" distribution of labeled aminoacids on the pH gradient, with single distributions of the "leading" and "trailing" species, suggested that pH gradients may form due to the zero mobility and low current zone at the gel termini occupied by isoelectric or uncharged non-amphoteric constituents. This hypothesis implied that pH gradient instability was due to constituent migration into the cathode and/or anode compartment, and, conversely, that pH gradient stability could be achieved under conditions such that the "leading" and/or "trailing" constituents carried no net charge, either through strict maintenance of an isoelectric pH if these species were amphoteric, or through protonation-deprotonation, if they are not. This aspect of the present invention deals with this hypothesis. In making the trailing and leading zones isoelectric, advantage was taken of the fact, recently described, that pH gradient formation and electrofocusing were feasible with buffer anolytes and catholytes.

The materials and methods employed were as follows:

(A). Buffer electrofocusing was carried out at 25° C. in polyacrylamide gels of 5%T, 15%$C_{DATD}$ containing the 0.01 M "standard amphoteric buffer mixture" as described in Nguyen, N.Y. and Chrambach, A., Anal. Biochem., 74, 145–153 (1976), except that aspartic acid and histidine were added to the gell buffer. Anolyte was 0.01 M aspartic acid (pI=2.98), catholyte 0.01 M histidine (pI=7.64). Control experiments were carried out with conventional anolyte and catholyte, 0.2 N $H_2SO_4$ and KOH. In this case, aspartic acid and histidine were not added to the gel buffer mixture. In one procedure, the aspartic acid in the gel was exchanged for asparagine (pI=4.30). In another procedure, 10.5 cpm/gel of $^{14}C$-aspartic acid and histidine were added to the polymerization mixture. Gel tubes were washed by soaking for several days in methanolic KOH, thorough rinsing to neutrality, immersion in 1% Gelamide 250 (American Cyanamid Co., Stamford, Conn.) draining onto tissue and drying at room temperature for several days. As a mechanical support, 0.5 ml of a 20%T, 2%C gel in the gel buffer described above was polymerized to give a plug at the bottom of the electrofocusing gel. Gels were loaded with 0.5–1 ml of BSA by underlayering of a sucrose-containing solution under the catholyte. pH Gradient analysis was carried out by the automatic device recently described in Chidakel et al., Anal. Biochem., 77, 216–225 (1976).

(B). Electrofocusing in polyacrylamide gels containing 1% Ampholine (pI=range 5–8) was carried out at 0°–4° C. as previously described in Baumann, G. and Chrambach, A., Progress in Isoelectric Focusing and Isotachophoresis, pp. 13–23, Elsevier, Excerpta Medica, N. Holland, Assoc. Sci. Pub., Amsterdam (1975) except: (a) with 0.2 N KOH as catholyte, 0.2 N $H_2SO_4$ as anolyte; (b) in gels of 5%T, 15%$C_{DATD}^{(c)}$ where indicated tubes were immersed in hexane with only the tube endings making contact with the anolyte and catholyte.

The results of the methods of Example V were as follows:

1. Stabilization of the pH gradient in buffer electrofocusing: Buffer electrofocusing was carried out at 25° C. with a mixture of twelve 0.01 M amphoteric buffers differing in pK, including histidine and aspartic acid. The anolyte was 0.01 M aspartic acid, the catholyte 0.01 M histidine. Both anolyte and catholyte were maintained at their isoelectric pH's of 2.98 and 7.64 by several exchanges of both with fresh solutions. pH Gradients measured as a function of time of electrofocusing remained constant within a random 0.5 pH unit fluctuation range, for a duration of electrofocusing of at least 100 hrs. The fluctuation range is the same as that of pH gradients determined by the same method at a single time of electrofocusing. For comparison, pH gradient instability at 0° C. in the same buffer mixture (except without aspartic acid and histidine) and with strongly acidic and basic anolyte and catholyte were determined. Table I shows the pH fluctuations of anolyte and catholyte as a function of electrofocusing time.

Table I

| Time (hrs) | | 0 | 1 | 18 | 22 | 27 | 43 | 70 | 90 | 120 |
|---|---|---|---|---|---|---|---|---|---|---|
| pH of Electrolyte | histidine (pI$_{25°C}$=7.64) | 7.64 | 7.64 | 8.10 CH | 7.67 | 7.80 CH | 7.90 CH | 7.60 | 7.67 | 7.70 |

Table I-continued

| | | | | | | | | | | |
|---|---|---|---|---|---|---|---|---|---|---|
| | aspartic acid (pI$_{25°\,C}$=2.98) | 2.98 | 2.96 | 2.92 | 2.95 | 3.00 | 2.95 | 2.95 | 3.06 | 2.96 |

| time (hrs) | | 0 | 1 | 29 | 39 | 50 | 69 | 111 | 116 | 135 |
|---|---|---|---|---|---|---|---|---|---|---|
| pH of | histidine (pI$_{25°\,C}$=7.64) | 7.64 | 7.64 | 8.10 CH | 8.10 CH | 8.10 CH | 8.10 CH | 8.10 CH | 8.20 CH | 8.20 |
| Electrolyte | asparagine (pI$_{25°\,C}$=4.30) | 4.30 | 4.30 | 4.15 CH | 4.15 CH | 4.35 | 4.35 | 4.27 | 4.25 | 4.35 |

| Time (hrs) | | 0 | 1 | 3 | 20 | 45 | 69 | 118 | 166 | 195 |
|---|---|---|---|---|---|---|---|---|---|---|
| pH of | lysine (pI$_{25°\,C}$=9.47) | 9.55 | 9.55 | 9.55 | 9.59 CH | 9.75 CH | 9.65 CH | 9.60 CH | 9.60 CH | 9.60 |
| Electrolyte | aspartic acid (pI$_{25°\,C}$=2.98) | 2.98 | 3.00 | 3.06 | 3.02 CH | 3.18 CH | 3.16 CH | 3.18 CH | 3.12 CH | 3.12 |

CH: exchange of Electrolyte

2. Stabilization of the cathodic drift of protein zones: Concurrently with maintenance of constant pH at the pI of anolyte and catholyte and resulting pH gradient stabilization, the cathodic drift of a zone of electrofocused BSA became negligible. This was demonstrated for application of either isoelectric aspartic acid or asparagine as anolyte. All other conditions were identical to those described for item No. 1 above.

3. Localization of aspartic acid and histidine at the gel and gradient termini: $^{14}$C-aspartic acid and -histidine concentrated at the gel and pH gradient termini, in agreement with previous data on aminoacid electrofocusing. After prolonged electrofocusing, the terminal labeled aminoacid peaks disappeared, presumably in view of exchange with unlabeled aminoacid from the adjacent large electrolyte reservoirs.

4. Measures providing improved wall adherence for electrofocusing gels: pH gradients were formed in pI-range 5-8 Ampholine between 0.2 N H$_2$SO$_4$ and KOH, using 1% Ampholine, 5%T, 15%C$_{DATD}$ gels at 0°–4° C., with gels suspended in either the acid or the base. In the apparatus used, levels of catholyte and anolyte were equal, so that there was no net hydrostatic pressure on the gel. It was seen that, nonetheless, there was an effect of the polarity of the gel on the pH gradients: The gel immersed in acid appeared acidified relative to the gel immersed in base, and vice versa.

Tests were also carried out with methamolic KOH cleaned, Gelamide 250 coated tubes containing a 20%T, 2%C gel plug containing the buffer mixture or Ampholine. It was seen that when wall adherene is improved through use of these three measures, the polarity of the gel fails to exert any effect on the pH gradients.

5. The effect of polarity on pH gradients was not due to electrolyte entrance into the gel by fluid pressure: A comparison was made between pH gradients, taken at various times of electrofocusing, which were obtained with the gels immersed in strongly acidic anolyte and those immersed in hexane, with only the tip of the tubes reaching into the anolyte. All other conditions were identical. It was seen that no significant difference exists between pH gradients of the two cases at any one time point. The 20%T, 2%C gel plug in 0.2 N H$_2$SO$_4$ swells considerably during the course of electrofocusing and is progressively extruded from the gel tube with time.

Concerning the foregoing results, pH gradient instability and isoelectric precipitation have been the principal inherent defects of isoelectric focusing from its inception. The isoelectric precipitation problem has largely been overcome in practice by electrofocusing in gels rather than solution. Recently, some initial attempts have been made to apply gel electrofocusing preparatively. However, the other problem, gradient instability, has been resisting a solution obstinately for many years. Numerous hypotheses have been raised and tested to account for it but have failed to resolve it. Among the more prominent examples, it has been shown that water accumulation at the gel center with backflow towards the periphery did not occur; that electroendosmotic flow could not account for more than 10% of the Ampholine migration into the electrolyte chambers during electrofocusing; that diffusion of Ampholine into the chambers was negligible; that reaction with a component of the polymerization reaction giving rise to crosslinked polyacrylamide was not a likely cause since it occurred in sucrose solution as well as in polyacrylamide; and that it was independent of the distance of the electrodes from the gel. Deficiency of neutral Ampholine components seemed not to be involved in pH gradient decay since substitution of Ampholine by a small number of well characterized, chemically stable, amphoteric buffers (or non-amphoteric buffers) in electrofocusing between strongly acidic and basic electrolytes did not abolish pH gradient instability. In fact, such substitution tended to accentuate gradient decay in inverse relation to the concentration of the gel buffer mixture, as discussed in Nguygen, N.Y. and Chrambach, A., *Anal. Biochem.*, 74, 145–153 (1976).

The fact that non-amphoteric amine buffers in an electrofocusing system between strongly acidic and basic electrolytes did not migrate through the gel tube unobstructedly but rather did form a steady-state, natural pH gradient required the postulation of the existence, at the gel termini, of a zero-mobility, low current "constituent barrier", which, presumably through operation of the laws of electroneutrality and mass conservation, and possibly through "regulation" as a "leading constituent" to zero mobility in a fashion analogous to isotachophoresis, prevents the passage of constituents internal to the pH gradient system into the adjacent electrolyte reservoir. The "zero-mobility" zone was conceived as either being isoelectric, in case of an amphoteric terminal constituent, or deprotonated, in case of a non-amphoteric amine in the terminal cathodic position of the pH gradient (or protonated in the case of a non-amphoteric acid in the terminal anodic position). This notion implied that pH gradient decay arose from the charging of the terminal constituent, either through operation of the mass law, or by a pH in the adjacent electrolyte chamber which was non-isoelectric with regard to the terminal constituent. The fact that an increase in the concentration of the adjacent buffer electrolyte by a factor of 75 stabilized the pH gradient seemed to lend some credence to the hypothesis. The fact, shown in this discussion, that maintenance of an electrolyte at a pH isoelectric to the terminal constituent also stabilizes the pH gradient to an unprecedented degree also corroborates the hypothesis.

The stabilization of pH gradients for at least 100 hours at 25° C. achieved in the present method, is equivalent to a stabilization for twice that length of time at 0° C. The reason for conducting the study at 25° C. was the unavailability of 0° C. pI values for the constituents. This stabilization is of practical relevance since it allows one to maintain electrofocusing gels at the steady-state in the laboratory for relatively long times ready for sample application and rapid electrofocusing of proteins. Gradient stabilization is also relieving the time pressure from electrofocusing analyses, making it possible to obtain equivalent data over extended periods of electrofocusing. Stability of pH gradients is also important for the physical-chemical and mechanistic study of electrofocusing.

pH Gradient stabilization with Ampholine containing gels is presently under investigation. Ampholine containing systems do present additional problems since defined and homogeneous terminal constituents are not available for any one pI-range of Ampholine. A surprising and unexplained finding of this method was that of pH gradient dependence on polarity, concomitant with the immersion of the gel in either acid or base, respectively. Since the apparatus provided hydrostatic equilibration, since replacement of acid in the lower reservoir by hexane had no effect on the pH gradient, it is quite unlikely that this dependence of gradients on polarity had anything to do with fluid pressure. The fact that this dependence is abolished by measures tending to improve wall adherence of the gel suggests a capillary effect by which the lower electrolyte enters into the gel tube along the walls. But it cannot be explained why such capillary flow would not proceed from the upper reservoir as well.

Undirectional effects as this would suggest some electroendosmotic mechanism. This has been ruled out as being insignificant relative to the cathodic drift but may be operative in polarity dependence. From a practical viewpoint, the problem of polarity dependence has been solved by the measures designed to improve wall adherence. However, these are a considerable practical inconvenience. It remains to be seen whether these measures can be simplified, and whether the polarity dependence also occurs in flat bed slab apparatus, or in apparatus with very shallow acid and base reservoirs. It also remains to be seen whether the problem exists to a practical extent when strongly acidic and basic anolyte and catholyte are replaced by buffers.

EXAMPLE VI

In another aspect of the present invention, pH gradients formed by Ampholine (pI-range 6–8) have been stabilized. Stability with time was achieved through equalization of the anolyte pH with the pH of the most acidic pI of the selected continuous pI-range. When the anolyte pH was reduced below this value, the hitherto unavoidable cathodic drift of the pH gradient with time ensued. The pH of the catholyte appears of little if any consequence for the stability or drift of the pH gradient. An increase in the concentration of anolyte and catholyte stabilized pH gradients formed by Ampholine in the same fashion as noted previously with regard to pH gradients formed by buffers.

The cathodic drift of pH gradients in isoelectric focusing has been a problem in the mechanistic understanding of isoelectric focusing for several years. To a lesser degree, it has also been a practical problem in protein resolution by isoelectric focusing, insofar as it produced decreasing resolution with time of electrofocusing and therefore forced one to investigate separations in electrofocusing as a function of time. The cathodic drift also accentuated the need for gel "nonrestrictiveness", when electrofocusing was carried out on polyacrylamide gels, since a very slow approach towards the isoelectric position often exceeded the time of optimal resolution. The drift also made it impossible to maintain pH gradients at the steady-state over extended periods, apply the sample to preformed pH gradients, and thereby to shorten the time of protein analysis by the time required for pH gradient formation.

Recently, the problem of pH gradient instability has been solved for pH gradients made in mixtures of simple buffers. Stable pH gradients were obtained in buffer electrofocusing (BEF) whenever the pH's of the cathodic and anodic electrolytes equalled those at the pH gradient termini. However, it was not possible at that time to demonstrate pH gradient stability with Ampholine (pI-range 3.5–10) using the same electrolytes as used for stabilization of the much narrower pI-range buffer pH gradient. In hindsight, this was presumably due to failure in providing the same equality of pH between gel termini and electrolytes which had been provided in the analogous experiment carried out with buffer pH gradients. The expectation at that time, that pH equalization would ensue with time and many changes of catholyte and anolyte by the constituent displacement mechanism described previously may have been fallacious. This discrepancy has now been remedied by a demonstration that identical conditions of pH gradient stabilization apply to pH gradient formed by Ampholine and to buffer pH gradients, as would be expected from the physical-chemical identity between buffers, at least the amphoteric ones, and Ampholine components.

The materials and methods employed were as follows:

(A). Hemoglobin was a human hemolysate (approximately 50 mg/ml), less than 2 weeks old, obtained from Ms. Minna Feld (Clinical Pathology Department, Clinical Center, NIH). Ampholine (pI-range 6–8) was obtained from LKB. Aminoacids were from Sigma. Basic aminoacids were obtained in the free base form. All aminoacid solutions were made in water without any pH adjustment. Aminoacids labeled with $^{14}C$ were admixed to Ampholine at 0.01 M final concentration.

(B). Electrofocusing: Gel electrofocusing was carried out in gels of 5%T, 15%$C_{DATD}$ at 0°–4° C., using 1% Ampholine in the pI-range 6–8 with addition of $^{14}C$-tyrosine (pI 5.63), serine (pI 5.68), phenylalanine (pI 5.91), valine (pI 6.00), isoleucine (pI 6.04), alanine (pI 6.11), glycine (pI 6.20), proline (pI 6.30) and histidine (pI 7.64), (but not the same $^{14}C$-labeled aminoacids used as anolyte and catholyte) at a final concentration of 0.01 M, and using the Pyrex apparatus and the procedures of polymerization of electrofocusing previously described, for example, in Chrambach, et al., *Ann. N.Y. Acad. Sci.*, 209, pp. 44–64 (1973). Gelamide 250 coated tubes were employed, as was a nylon mesh gel support. Aminoacid solutions were used as catholyte and anolyte as described hereinafter.

(C). pH Gradient measurements: pH Gradients were determined by the automated device mentioned previously.

(D). Isotope analysis: $^{14}C$-labeled aminoacids were determined in catholyte and anolyte at various electrofocusing times as described hereinafter. At each time, 1 ml was mixed with 15 ml Aquasol, left to stand at 4° C. at least overnight in the dark and counted in a liquid scintillation spectrometer at room temperature.

The results of the methods of Example VI were as follows:

1. Stabilization of a pH gradient made in Ampholine: Electrofocusing of hemoglobin was carried out in a pH gradient formed by pI-range 6-8 Ampholine and 0.01 M aminoacids labeled with $^{14}C$ between 0.01 M histidine (catholyte, $pH_{25°}$ C. = 7.64) and threonine (anolyte, $pH_{25°}$ C. = 5.59). The pH gradient was stable for 170 hours. Labeled aminoacid constituents of the pH gradient were not significantly released into the electrolytes. During electrofocusing, the pH's of anolyte and catholyte were constant at 7.69 ± 0.08 and 5.89 ± 0.37, respectively. The relative postion of the hemoglobin zone on the pH gradient remained constant for 170 hrs. at pH 6.9–7.1, close to the isoelectric point of the protein of 6.8–6.9.

An analogous demonstration of pH gradient stability was made under identical conditions except for the use of 0.01 M glycine (pH 6.20) as the anolyte. The pH's of anolyte and catholyte were constant at 7.76 ± 0.09 and 6.14 ± 0.19. This pH gradient and the hemoglobin position on the gel (pH 6.9–7.2) were constant for 110 hours.

2. Catholyte effect on stability: A graph was prepared showing the time course of the same electrofocusing experiment as described in item No. 1 except that the catholyte was made 0.01 M lysine ($pH_{25°}$ C. = 9.47). Another graph was prepared, showing the time course of the pH gradient and demonstrating its relative instability. Migration of labeled aminoacid constituents into catholyte and anolyte still appeared negligible. Catholyte and anolyte pH's were invariant at 9.61 ± 0.08 and 5.66 ± 0.17. Hemoglobin positions relative to the gel were constant for 70 hours but drifted cathodically thereafter.

3. Cathodic drift: By lowering the pH of the anolyte to 3.1 by choice of isoelectric glutamic acid, and keeping all other conditions the same as in the experiment described in item No. 1, an immediate and persistent cathodic drift of the pH gradient resulted. Again, labeled aminoacid constituents did not migrate out of the gel at a significant rate. Catholyte and anolyte pH's were invariant within 7.74 ± 0.09 and 3.18 ± 0.08. Isoelectric protein postions drifted cathodically.

4. Stabilizing effect of the concentration of anolyte and catholyte: The experiments described in item No. 2 were repeated, using 0.1 M anolyte and catholyte. Also, the experiments described in item No. 3 were repeated with 0.04 M electrolytes. Increasing anolyte and catholyte concentrations ten and four-fold respectively had a stabilizing effect on the pH gradients.

From the foregoing results, it is seen that there has been remedied an inherent defect of isoelectric focusing with which it had been afflicted since its inception, i.e., pH gradient instability and the "cathodic drift".

It is now possible to maintain the steady-state pH gradient formed by Ampholine for at least as long as a week, as compared to a few hours in conventional gel electrofocusing carried out between strong acid and base, such prior art methods having been described in McCormick et al., *Anal. Biochem.*, 75, pp. 314–324 (1976). Thus, it is possible to have a steady-state pH gradient waiting for sample application during this time, thereby reducing the time required for isoelectric focusing by the time required to reach the steady-state. This time saving is substantial, in particular, when high concentrations of Ampholine or very flat pH gradients are used, as can be formed by commercial wide Ampholine pI-ranges by reducing the pH (and pI) difference between catholyte and anolyte. Another practical advantage of gradient stability is the possibility to monitor pH constancy over extended time periods and thereby to establish, by intrapolation, the apparent pI values for a protein. For mechanistic and physical-chemical studies gradient stability is an obvious prerequisite.

Stability of pH gradients has been achieved by pH control of the anolyte. Surprisingly, the choice of pH of the catholyte seemed of little effect on the stability of the pH gradient investigated. This suggests another point of analogy between isotachophoresis and electrofocusing: regulation of all constituents to zero mobility appears a function of the leading consitituent, as would be expected from an isotachophoretic mechanism.

A factor which is related to the much greater effectiveness of anolyte, as compared to catholyte, in regulating the pH gradient drift, is the fact that cathodic drifts are predominant. Incidents of anodic drift seem comparatively second-order and transient. During relatively short time periods, of the order of 48 hour periods, anodic pH gradient drifts can be observed, but they revert to the cathodic direction, and are therefore interpreted as transient, although possibly mechanistically interesting phenomena.

Failure to demonstrate a consistent "anodic drift" makes it particularly important to draw a clear distinction between the "pH gradient drift" in electrofocusing and what may be called the "constituent displacement" mechanism. The term "drift" is being used to describe the movement of the entire, intact pH gradient, and the progressive migration of its constituents into the cathode compartment. In contrast, the term "constituent displacement" is reserved for the case in which selected constituents, representing only part of the pH gradient, are forced to migrate into one of the electrolyte chambers by the mechanism mentioned previously. Thus anodic constituent displacement exists and has been used effectively for zone mobilization while a constituent anodic drift has not been demonstrated to date. The possibility to stabilize pH gradients in electrofocusing still leaves the problem of the mechanism of pH gradient formation and decay fully open, although it simplifies the experimental system for the study of the mechanism involved.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. In a method of isoelectric focusing between acid anolyte and basic catholyte, the improvement which comprises forming a pH gradient in a mixture of a plurality of buffers located in the field between said anolyte and said catholyte, wherein the a acid anolyte and basic catholyte are replaced by the leading and trailing buffers of the buffer mixture, possessing the lowest and highest $pK_2$ values of the buffer mixture.

2. The method of claim 1, wherein the buffer anolyte and catholyte are made 50% in sucrose.

3. The method of claim 1, wherein the buffer anolyte and catholyte are present in a concentration of 0.75 M.

4. In a method of isoelectric focusing between acid anolyte and basic catholyte, the improvement which comprises forming a pH gradient in a mixture of a plurality of buffers located in the field between said anolyte and said catholyte, wherein the acid anolyte and basic catholyte are replaced by isoelectric buffers identical to the terminal constituents of the pH gradient and gel.

5. In a method of isoelectric focusing between acid anolyte and basic catholyte, the improvement which comprises forming a pH gradient in a mixture of a plurality of buffers located in the field between said anolyte and said catholyte, wherein the pH of the anolyte is equalized with the pH of the most acidic pI of the selected continuous pI range.

* * * * *